United States Patent
Wilke et al.

(10) Patent No.: US 11,181,460 B1
(45) Date of Patent: Nov. 23, 2021

(54) APPARATUS AND METHOD FOR MEASURING PERMEATION OF CONTAMINANTS THROUGH A COMPLEX PROTECTIVE MATERIAL SWATCH

(71) Applicant: Combat Capabilities Development Command, Chemical Biological Center, Apg, MD (US)

(72) Inventors: Douglas E Wilke, Joppa, MD (US); Terrence G D'Onofrio, Bel Air, MD (US); Christopher B. Steinbach, Phoenix, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 62 days.

(21) Appl. No.: 16/903,729

(22) Filed: Jun. 17, 2020

Related U.S. Application Data

(60) Provisional application No. 62/864,069, filed on Jun. 20, 2019.

(51) Int. Cl.
*G01N 15/08* (2006.01)
*G01N 11/08* (2006.01)

(52) U.S. Cl.
CPC ......... *G01N 15/0806* (2013.01); *G01N 11/08* (2013.01)

(58) Field of Classification Search
CPC .... G01N 33/367; G01N 15/082; G01N 33/36; G01N 17/002
See application file for complete search history.

(56) References Cited

U.S. PATENT DOCUMENTS

| | | | | |
|---|---|---|---|---|
| 2,012,762 A | * | 8/1935 | Kern | G01N 33/367 |
| | | | | 73/159 |
| 2,755,660 A | * | 7/1956 | Kammermeyer | G01N 15/0826 |
| | | | | 73/38 |
| 3,248,930 A | * | 5/1966 | Speegle | G01N 15/0826 |
| | | | | 73/38 |

(Continued)

FOREIGN PATENT DOCUMENTS

| | | | | |
|---|---|---|---|---|
| DE | 4400226 A1 | * | 7/1995 | ............. G01N 17/00 |
| WO | WO-0028300 A1 | * | 5/2000 | ........... G01N 15/082 |
| WO | WO-2019025969 A1 | * | 2/2019 | ........... B01D 63/087 |

*Primary Examiner* — David A. Rogers
(74) *Attorney, Agent, or Firm* — Ulysses John Biffoni

(57) ABSTRACT

A test cell may include a base frame including a test slot; a pressure-generating insert positioned on a pedestal within the test slot; an impermeable protective layer in contact with the base frame; a sorbent layer positioned between the pressure-generating insert and the impermeable protective layer; a complex protective material swatch in contact with the sorbent layer, the complex protective material swatch having a contaminant applied thereon; a locking frame in contact with the impermeable protective layer, wherein the locking frame secures the impermeable protective layer to the base frame; a sealing gasket in contact with at least the locking frame and the complex protective material swatch; a gasket compression frame in contact with the sealing gasket; a cover in contact with the stability plate; and weights in contact with the cover. The test cell may be included in methods for measuring permeation of contaminants through complex protective material swatches.

20 Claims, 2 Drawing Sheets

(56) References Cited

U.S. PATENT DOCUMENTS

| | | | | |
|---|---|---|---|---|
| 3,378,481 A | * | 4/1968 | Saravis | G01N 27/44704 204/641 |
| 3,577,767 A | * | 5/1971 | Stedile | G01N 15/0826 73/38 |
| 3,710,945 A | * | 1/1973 | Dismore | B01D 63/022 210/321.63 |
| 4,050,995 A | * | 9/1977 | Bredeweg | G01N 27/42 205/788 |
| 4,298,345 A | * | 11/1981 | Sodickson | G01N 33/528 422/420 |
| 4,385,517 A | * | 5/1983 | Sorce | G01N 15/0826 73/38 |
| 4,468,951 A | * | 9/1984 | Garcia | G01N 15/08 73/38 |
| 4,493,815 A | * | 1/1985 | Fernwood | B01D 61/18 210/232 |
| 4,854,157 A | * | 8/1989 | Wilson | G01N 15/0826 73/38 |
| 5,081,863 A | * | 1/1992 | Reid | G01N 15/08 73/38 |
| 5,188,733 A | * | 2/1993 | Wang | B01J 19/0046 210/321.84 |
| 5,265,463 A | * | 11/1993 | Loebig | G01N 15/082 73/23.2 |
| 5,376,554 A | * | 12/1994 | Vo-Dinh | A62D 5/00 436/104 |
| 5,591,636 A | * | 1/1997 | Grass | B01D 61/18 324/450 |
| 5,633,453 A | * | 5/1997 | Johnson | G01N 15/08 73/38 |
| 5,659,130 A | * | 8/1997 | Chung | G01N 15/08 422/401 |
| 5,792,430 A | * | 8/1998 | Hamper | B01J 19/0046 422/131 |
| 5,866,801 A | * | 2/1999 | Johnson | G01N 15/08 73/38 |
| 6,043,027 A | * | 3/2000 | Selick | B01L 3/5025 422/417 |
| 6,435,007 B1 | * | 8/2002 | Smith | G01N 7/10 73/31.05 |
| 6,439,036 B1 | * | 8/2002 | Mansky | B01J 19/0046 73/159 |
| 6,455,007 B1 | * | 9/2002 | Mansky | B01J 19/0046 422/553 |
| 6,662,635 B2 | * | 12/2003 | Mansky | B01J 19/0046 422/503 |
| 6,878,344 B2 | * | 4/2005 | Mansky | B01J 19/0046 422/503 |
| 6,993,956 B2 | * | 2/2006 | Bouten | G01N 15/1227 73/40 |
| 7,635,452 B2 | * | 12/2009 | Roscoe | B01L 3/5025 422/50 |
| 8,603,825 B2 | * | 12/2013 | Chua | G01N 15/0826 436/5 |
| 9,016,112 B2 | * | 4/2015 | Paz | G01N 5/025 73/73 |
| 9,021,865 B1 | * | 5/2015 | D'Onofrio | G01N 15/08 73/38 |
| 9,190,688 B2 | * | 11/2015 | Hwang | H01M 8/04 |
| 9,364,174 B2 | * | 6/2016 | Lin | G01N 27/327 |
| 9,400,233 B2 | * | 7/2016 | Lin | G01N 33/66 |
| 9,594,010 B1 | * | 3/2017 | D'Onofrio | G01N 15/082 |
| 9,979,032 B2 | * | 5/2018 | Hwang | H01M 8/04313 |
| 11,085,867 B1 | * | 8/2021 | Ruppert | G01N 15/082 |
| 2002/0168293 A1 | * | 11/2002 | Smith | G01N 33/367 422/68.1 |
| 2009/0320564 A1 | * | 12/2009 | Piombini | G01N 15/0826 73/38 |
| 2014/0134607 A1 | * | 5/2014 | Lin | G01N 33/5438 435/5 |
| 2014/0223999 A1 | * | 8/2014 | Graehlert | G01N 15/0806 73/38 |
| 2016/0036069 A1 | * | 2/2016 | Hwang | H01M 8/04 429/495 |
| 2016/0370362 A1 | * | 12/2016 | Lin | G01N 33/54366 |
| 2018/0015424 A1 | * | 1/2018 | Exley | B01D 67/009 |

\* cited by examiner

APPARATUS AND METHOD FOR MEASURING PERMEATION OF CONTAMINANTS THROUGH A COMPLEX PROTECTIVE MATERIAL SWATCH

CROSS-REFERENCE TO RELATED APPLICATION

This application claims priority to U.S. Provisional Patent Application No. 62/864,069 filed on Jun. 20, 2019, which is incorporated herein by reference in its entirety.

GOVERNMENT INTEREST

The embodiments herein may be manufactured, used, and/or licensed by or for the United States Government.

TECHNICAL FIELD

The embodiments herein generally relate to quantitative permeation testing for personal protective equipment (PPE) contact scenarios including quality controls and environmental controls.

BACKGROUND

Multiple methods exist for measuring permeation through protective equipment. According to the U.S. Army Test Operating Procedure (TOP), the method depends on the physical state of the contaminant, and the detection method. For liquid-contamination-vapor-detection, the suggested method was the Aerosol Vapor Liquid Assessment Group (AVLAG) test cell. This apparatus uses a vapor detection scheme with an air sweep under the test swatch to gather the vapor of permeated contaminant. Detection may utilize MINICAMS® monitoring systems (available from OI Analytical, Texas, USA), sorbent tubes, or bubblers to collect the vapor. This method permits time-resolved quantification of vapor breakthrough and environmental control. However, this method allows for the quantification of the vapor phase only, requires the use of flat swatches, and generally requires a cumbersome setup. Accordingly, this method requires a relatively significant investment in infrastructure for proper operation.

For liquid-contamination-liquid-detection, the TOP suggests using an expulsion method. This method achieves low costs for setup and operation, time-resolved detection, application of realistic forces, and simplicity. However, this method requires bulk-liquid breakthrough for detection, and results in lack of environmental control and a lack of quantification when detector paper is used. Moreover, the TOP provides limited guidance on quantifying breakthrough using this method.

In 2007, a permeation program was initiated to examine the performance of personal protective equipment (PPE) against contaminants. Given the low volatility of the test compounds, the vapor detection method was deemed insufficient. Furthermore, the liquid-contamination-liquid-detection precludes quantification of breakthrough. Therefore, a hybrid method was devised to enable quantification of breakthrough in a contact scenario, with environmental control. This method uses a sorbent pad under the test swatch within an AVLAG cell. The swatch is contaminated in accordance with the TOP, and at a chosen time point, the swatch is removed from the cell, and the sorbent pad is extracted. The extractant is analyzed to quantify breakthrough. As part of the testing, a divinylbenzene (DVB) pad is characterized for extraction efficiency. However, this method produces a variable level of contact between the swatch and sorbent pad. This is exacerbated with non-flat swatches taken from fingers of gloves, or folded portions of protective suits. Furthermore, there is no practical method to apply relevant forces of contact. Finally, the use of the AVLAG makes this system cumbersome and each swatch is limited to a single time point.

The need for the contact scenario has been demonstrated toxicologically with rabbits during a separate study. The rabbit study used a latex swatch, known to be permeable to the nerve agent VX, as the swatch test material. The swatch was either in direct contact with the rabbit skin, or elevated by 1 cm off the skin. The elevated scenario represented a vapor only condition for exposure. The same conditions were used in both cases with regard to skin condition, contamination density, contact time, and test material. Data collected included onset of toxic signs, time-resolved acetyl cholinesterase (AChE) enzymatic activity level, and quantitation of regenerated VX in the skin and blood. All rabbits in the direct-contact scenario died, while no signs to mild signs were observed in the vapor-only rabbits. The exposure level is further supported by AChE activities. Furthermore, the level of agent measured in the skin was several orders of magnitude greater for the rabbits in the direct-contact configuration. Given that gloves and other personal protective equipment (PPE) are in direct contact with the skin, there was a need to develop additional testing techniques and systems that enables quantification in a direct contact configuration.

With this understanding, an apparatus and corresponding methods were developed for testing the permeability of two-inch circle swatches of bulk material for their chemical protection properties. Such an apparatus and methods are disclosed in U.S. Pat. No. 9,021,865, which is incorporated herein by reference in its entirety. However, the apparatus and methods disclosed in U.S. Pat. No. 9,021,865 are not capable of testing complex protective material swatches, such as swatches that include seams, closures, zippers, and the like. Currently, the only methods of testing complex protective material swatches is with a mannequin or a volunteer. However, it is not always possible to determine the impact of a complex interface as the contamination could spread making discrete localization difficult. Furthermore, it is not currently possible to determine the contact transfer of low-volatility contaminants that break through the interfaces. Given these shortcomings in the art, apparatuses and methods for measuring permeation of contaminants through complex protective material swatches is desirable.

SUMMARY

The following summary is provided to facilitate an understanding of some of the innovative features unique to the present disclosure and is not intended to be a full description. A full appreciation of the various aspects of the disclosure can be gained by taking the entire specification, claims, drawings, and abstract as a whole.

It is highly desirable that a test cell be capable of measuring permeation of a contaminant through a complex protective material swatch. Such a test cell must provide even pressure between the complex protective material swatch and a sorbent layer such that no gaps are formed during testing. Moreover, the test cell must effectively isolate the complex protective material swatch to prevent cross-contamination on a sorbent layer that is in contact with, and positioned below, the complex protective material swatch during testing. Finally, the results of testing the complex protective material swatch should be similar to those provided when a standard, flat, air-permeable swatch is tested using more typical test cells and methods.

In one or more embodiments, a test cell for measuring permeation of a contaminant through a complex protective material swatch may include a base frame comprising a test slot; a pressure-generating insert positioned on a pedestal within the test slot: a sealing plate in contact with the base frame; an impermeable protective layer in contact with the sealing plate, the impermeable protective layer including a flexible material and configured to prevent the contaminant from contaminating the pressure-generating insert; a sorbent layer positioned on a top surface of the impermeable protective layer; a complex protective material swatch in contact with the sorbent layer; a locking frame in contact with the impermeable protective layer and configured to secure the impermeable protective layer to the locking frame and sealing plate; a sealing gasket in contact with at least the locking frame and the complex protective material swatch; a gasket compression frame in contact with the sealing gasket, the gasket compression frame configured to compress the sealing gasket between the gasket compression frame and the sealing plate; a cover in contact with the gasket compression frame, the cover configured to allow for dosing the complex protective material swatch with the contaminant; and one or more weights in contact with the cover, the one or more weights causing evenly pressurized contact between the complex protective material swatch and the sorbent layer in order to determine the level of permeation of the contaminant through the complex protective material swatch.

In one or more embodiments, a method for measuring permeation of a contaminant through a complex protective material swatch may include providing a base frame comprising a test slot, wherein a pressure-generating insert is positioned on a pedestal within the test slot; placing a sealing plate on the base frame; securing an impermeable protective layer to the sealing plate with a locking frame; placing a sorbent layer on the impermeable protective layer; placing the complex protective material swatch on the sorbent layer; placing a sealing gasket on at least the locking frame and the complex protective material swatch; placing a gasket compression frame on the sealing gasket; compressing the sealing gasket between the gasket compression frame and the sealing plate, thereby sealing the test cell; dosing the complex protective material swatch with the contaminant; placing a cover on the gasket compression frame; applying one or more weights to the cover, thereby causing evenly pressurized contact between the complex protective material swatch and the sorbent layer; and measuring a level of contamination of the sorbent pad upon exposure to the complex protective material swatch.

In one or more embodiments, a test cell may include a base frame including a test slot; a pressure-generating insert positioned on a pedestal within the test slot; an impermeable protective layer in contact with the base frame; a sorbent layer positioned between the pressure-generating insert and the impermeable protective layer; a complex protective material swatch in contact with the sorbent layer, the complex protective material swatch having a contaminant applied thereon; a locking frame in contact with the impermeable protective layer, wherein the locking frame secures the impermeable protective layer to the base frame; a sealing gasket in contact with at least the locking frame and the complex protective material swatch; a gasket compression frame in contact with the sealing gasket; a cover in contact with the stability plate; and one or more weights in contact with the cover.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

For the purpose of illustrating the concepts described in the present disclosure, there is shown in the drawings a form that is exemplary: it being understood, however, the present disclosure is not limited to the precise arrangements and instrumentalities shown. The drawings are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention. Exemplary aspects will become more fully understood from the detailed description and the accompanying drawings wherein.

DETAILED DESCRIPTION

Figure 1:
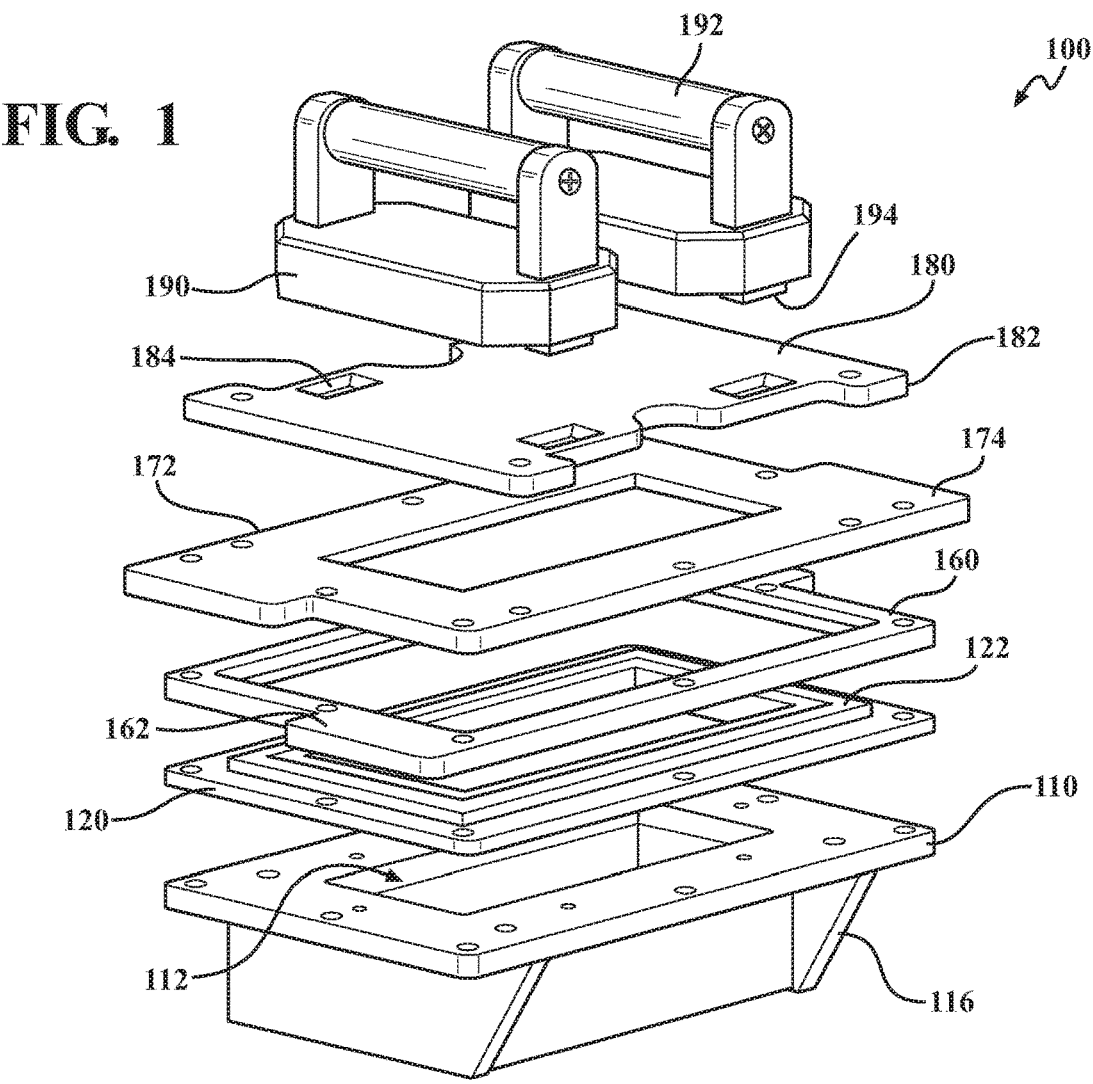
FIG. 1 is an exploded view of a test cell, according to one or more embodiments presently presented.

Detailed aspects are disclosed herein; however, it is to be understood that the disclosed aspects are merely exemplary in nature and may be embodied in various and alternative forms. The figures are not necessarily to scale. Therefore, specific details disclosed herein are not to be interpreted as limiting, but merely as a representative basis for any aspect of the invention and/or as a representative basis for teaching one skilled in the art to variously employ the present invention.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Throughout this specification, where publications are referenced the disclosures of these publications in their entireties are hereby incorporated by reference into this application to more fully describe the state of the art to which this invention pertains.

The following terms or phrases used herein have the exemplary meanings listed below in connection with at least one aspect:

The term "low-volatility substance," as used herein, means a substance with a vapor pressure less than 10 Pa at 20° C.

The embodiments herein provide a test method and test cell for measuring permeation of a contaminant through a complex protective material swatch. The test method increases the confidence of quantitative permeation test results for the contaminant, increases throughput, and reduces operational testing costs by improving controls over various quantitative measurements and environmental test conditions. The method and test cell also evaluate complex protective material swatch under conditions that reflect more realistic use in real-world environmental scenarios, such as mimicking forces associated with touching a contaminated surface or grasping a contaminated object.

Referring now to FIGS. 1-4, a test cell 100, according to one or more embodiments, is shown. The test cell 100 may include a base frame 110 including a test slot 112. In one or more embodiments, the base frame 110 may further include one or more triangular guides 116 configured to allow the test cell 110 to be positioned at a slanted angle. A pressure-generating insert 114 may be positioned on a pedestal 111 within the test slot 112. A sealing plate 120 may be in contact with the base frame 110. An impermeable protective layer 130 may be in contact with the sealing plate 120 and configured to prevent a contaminant from contaminating the pressure-generating insert 114. A sorbent layer 140 may be positioned on a top surface 132 of the impermeable protective layer 130. A complex protective material swatch 150 may be in contact with the sorbent layer 140. A locking frame 160 may be in contact with the impermeable protective layer 130 and configured to secure the impermeable protective layer 130 to the locking frame 160 and the sealing plate 120. A sealing gasket 170 may be in contact with at least the locking frame 160 and the complex protective material swatch 150. A gasket compression frame 172 may be in contact with the sealing gasket 170 and configured to compress the sealing gasket 170 between the gasket compression frame 172 and the sealing plate 120. A cover 180 may be in contact with the gasket compression frame 172 and configured to allow for dosing the complex protective material swatch 150 with the contaminant. One or more weights 190 may be in contact with the cover 180, the one or more weights 190 causing evenly pressurized contact between the complex protective material swatch 150 and the sorbent layer 140 in order to determine the level of permeation of the contaminant through the complex protective material swatch 150.

Figure 3:
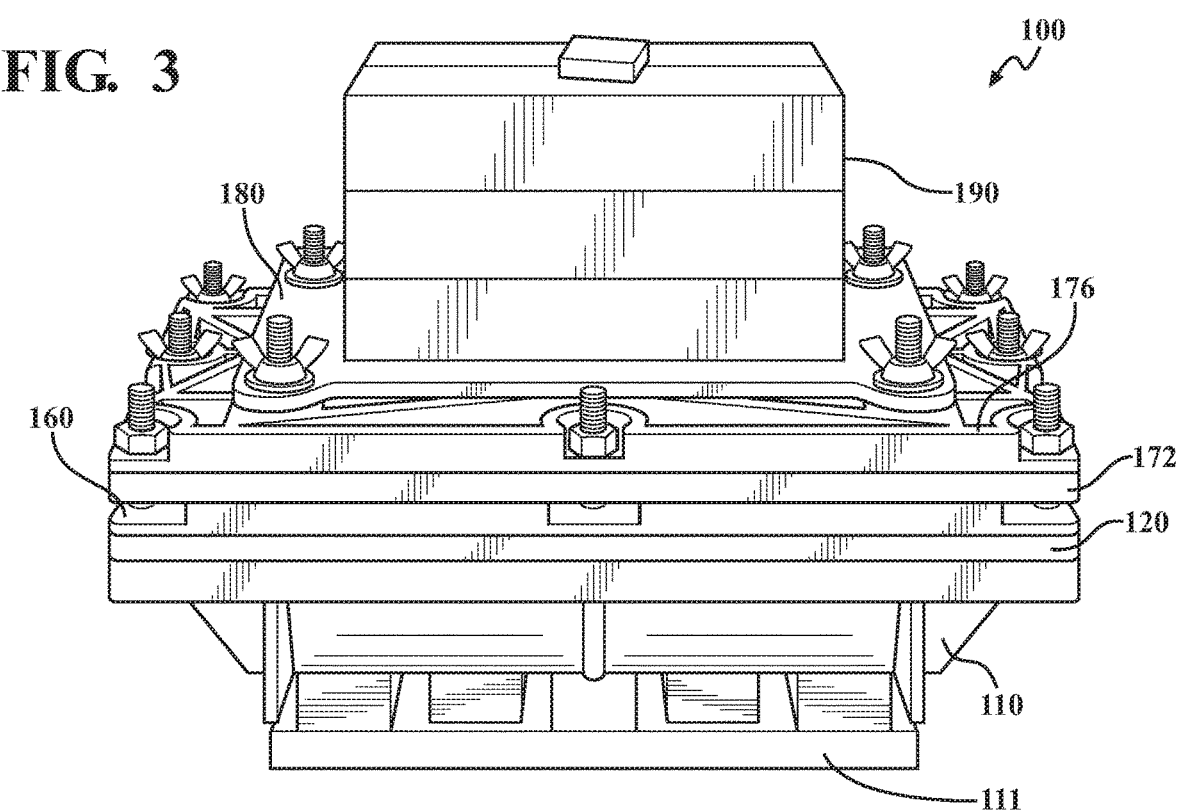
FIG. 3 is an illustration of a test cell, according to one or more embodiments presently presented.
Figure 4:
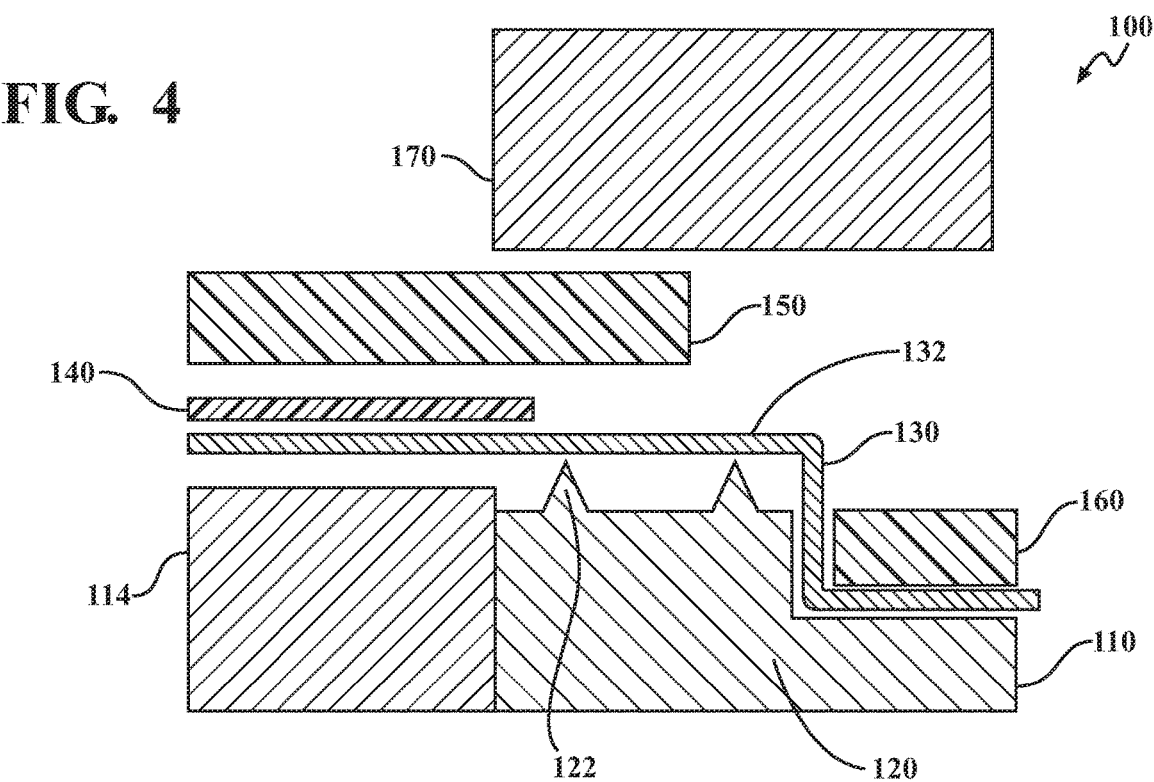
FIG. 4 is a cross-sectional view of a test cell, showing the interface of the swatch being tested within the test cell.

As shown in FIG. 3, the test cell 100 may include a stability plate 176 positioned between the gasket compression frame 172 and the cover 180. The stability plate 176 may provide additional structural integrity to the test cell 100. The stability plate 176 may be especially advantageous if one or more components of the test cell 100 are formed from plastic.

The pressure-generating insert 114 may be formed from a material that allows for even pressurization between the complex protective material swatch 150 and the sorbent layer 140 without causing gaps to form between the complex protective material swatch 150 and the pressure-generating insert 114. Suitable materials may include foams in which 0.2 pounds per square inch (psi) to 4 psi of pressure are needed to compress the foam by 25%. In embodiments, the pressure-generating insert 114 may include viscoelastic polyurethane foam, which is commercially available as Memory Foam. The viscoelastic polyurethane foam used to form the pressure-generating insert 114 may have a density from 1 pound per cubic foot ($lb/ft^3$) to 10 $lb/ft^3$.

In embodiments, the impermeable protective layer 130 may be formed from any chemically impermeable materials in order to prevent permeation of the contaminant through the complex protective material swatch 150 and into the pressure-generating insert 114. Suitable materials of the impermeable protective layer 130 may include butyl rubber, nitrile, neoprene, or combinations thereof. In one or more embodiments, the impermeable protective layer 130 may have a thickness from 1 mil to 20 mils, such as from 7 mils to 15 mils. Without being bound by theory, such a thickness range for the impermeable protective layer 130 is preferred as materials thinner than 1 mil may not provide the required chemical impermeability, while materials thicker than 20 mils may not have the flexibility to conform to the complex features of the complex protective material swatch 150. In one or more embodiments, an additional impermeable protective layer (not shown) may be placed between the sorbent layer 140 and the complex protective material swatch 150, which may assist during leak testing as described below.

In embodiments, the sealing plate 120 may include one or more sealing edges 122 to enhance the seal of the sealing gasket 170.

The sorbent layer 140 may be formed from any material capable of absorbing any contaminant permeating through the complex protective material swatch 150. Without being limited by theory, it is believed that the sorbent layer 140 may be formed from a wide variety of materials, which depend on the contaminant of interest. For example, the sorbent layer 140 may include one or more divinyl benzene pads if the contaminant of interest is an organophosphorus liquid, such as a nerve agent or a pesticide. Alternatives for the sorbent layer 140 include latex or synthetic skin. Choice of the ideal sorbent layer 140 will be dependent on the contaminant.

The complex protective material swatch 150 may include any material having a complex geometry with the potential to increase permeation of a contaminant through the swatch. Suitable complex protective material swatches may include any single or double-layer fabric swatch having a zipper, a hook and loop fastener, seams, hems, valve seats, pass-through fittings, electronic connectors, or combinations thereof.

The pressure applied to the complex protective material swatch 150 is relevant when determining whether complex protective material swatch 150 is permeable to the contaminant. According to the U.S. Army Test Operating Procedure, the applied weight of 1 psi is mandated and used during industrial hygiene studies documented in peer-reviewed journals as a "heavy touch," which includes touching a contaminated surface or grasping a contaminated object. The applied weight should also be applied such that the weight is evenly pressurized in order to avoid forming gaps between the complex protective material swatch 150 and the pressure-generating insert 114 during testing. As such, the one or more weights 190 cause evenly pressurized contact between the complex protective material swatch 150 and the sorbent layer 140 during testing.

In one or more embodiments, the one or more weights provide from 0.1 pounds per square inch (psi) to 5 psi of evenly pressurized contact between the complex protective material swatch 150 and the sorbent layer 140. In certain embodiments, the one or more weights provide from 0.2 psi to 4.5 psi, from 0.3 psi to 4 psi, from 0.4 psi to 3.5 psi, from 0.5 psi to 3 psi, from 0.6 psi to 2.5 psi, from 0.7 psi to 2 psi, from 0.8 psi to 1.5 psi, from 0.9 psi to 1.1 psi, or about 1 psi of evenly pressurized contact between the complex protective material swatch 150 and the sorbent layer 140.

In embodiments, the contaminant used for measuring permeation through the complex protective material swatch 150 may include a low-volatility substance, as defined above. Suitable low-volatility substances may include pesticides, industrial chemicals, nerve agents, and the like. In one or more embodiments, the low-volatility substance may include a V-series nerve agent.

As the test cell 100 may be used to test toxic contaminants, operators of the test cell may find themselves operating the test cell 100 with heavy gloves or in a controlled environment, such as a glove box or fume hood. In order to provide an operator with additional dexterity while manipulating the test cell 100, one or more of the components of the test cell 100 may include self-locating features and handles. In one or more embodiments, the one or more weights 190 may each include a handle 192 that provides a gripping point for an operator manipulating the test cell 100. The one or more weights 190 may also each include self-locating nubs 194 configured to attach to one or more tapered holes 184 located on the cover 180. The locking frame 160, the gasket compression frame 172, and the cover 180 may also include one or more tabs 162, 174, and 182, respectively, which collectively provide one or more additional gripping points for an operator manipulating the test cell 100.

The test cell 100, according to one or more of the previously described embodiments, may be incorporated in methods for measuring permeation of a contaminant through a complex protective material swatch. The method may include providing a base frame 110 comprising a test slot 112, wherein a pressure-generating insert 114 may be positioned within the test slot 112. The method may further include placing a sealing plate 120 on the base frame 110 and securing an impermeable protective layer 130 to the sealing plate 120 with a locking frame 160. The method may further include placing a sorbent layer 140 on the impermeable protective layer 130, placing a complex protective material swatch 150 on the sorbent layer 140, and placing a sealing gasket 170 on at least the locking frame 160 and the complex protective material swatch 150. The method may further include compressing the sealing gasket 170 between the sealing plate 120 and gasket compression frame 172, thereby sealing the test cell 100. The method may further include dosing the complex protective material swatch 150 with a contaminant and placing a cover 180 on the sealing gasket 170. The method may further include applying one or more weights 190 to the cover 180, thereby causing evenly pressurized contact between the complex protective material swatch 150 and the sorbent layer 140. The method may finally include measuring a level of contamination of the sorbent pad 140 upon exposure to the complex protective material swatch 150. In one or more embodiments, the method may also include positioning a stability plate 172 between the sealing gasket 170 and the cover 180.

EXPERIMENTAL

The various embodiments of present disclosure will be further clarified by the following examples. The examples are illustrative in nature, and should not be understood to limit the subject matter of the present disclosure.

Figure 2:
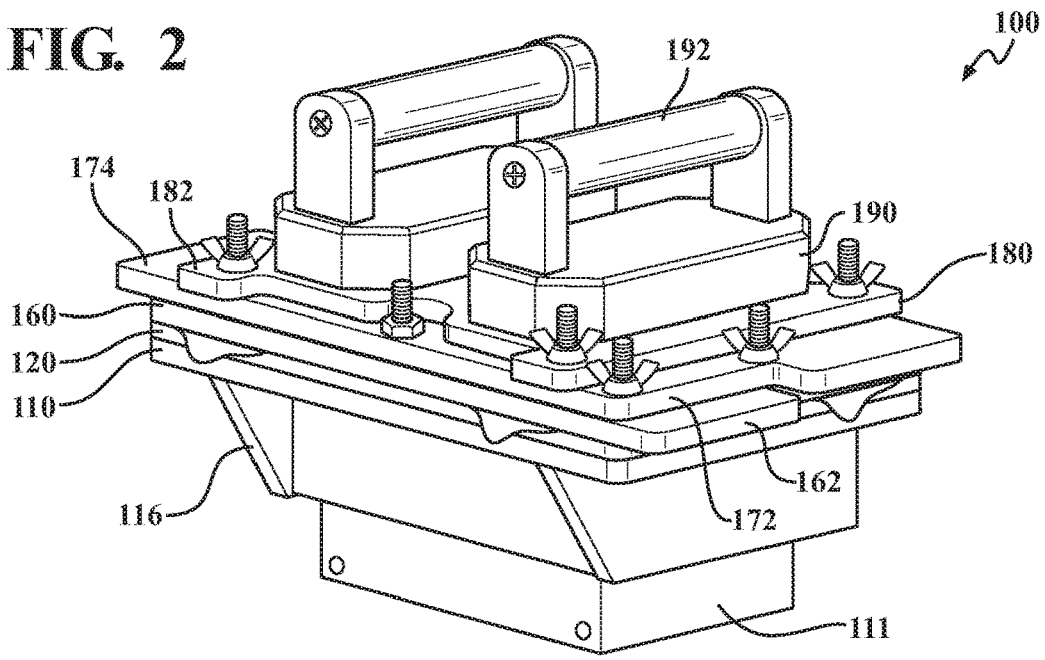
FIG. 2 is an illustration of a test cell, according to one or more embodiments presently presented.

Closed complex protective material swatches were tested with the test cells shown in FIGS. 2 and 3.

In a first test, permeability results of a complex protective material swatch tested with the experimental test cell shown in FIG. 3 were compared to those generated by a simple protective material swatch (e.g., a swatch of single-layer fabric) tested by a traditional low volatility agent permeation (LVAP) apparatus, such as the apparatus disclosed in U.S. Pat. No. 9,021,865. The comparative sample was prepared by dosing the simple protective material swatch with a total of 6×1 µL O-Ethyl S-(2-diisopropylaminoethyl) methylphosphonothioate (VX) droplets and using a single 47 mm diameter DVB pad as the sorbent layer. After dosing, the traditional LVAP apparatus was sealed for 24 hours at 1 psi. Upon completion, the traditional LVAP apparatus was disassembled, and the DVB pad was individually extracted and analyzed via Liquid Chromatography-Triple Quadrupole Mass Spectrometry (LC-MS/MS) analysis for breakthrough of VX through the simple protective material swatch. This comparative test was repeated five times.

Meanwhile, a complex protective material swatch was tested with the experimental test cell shown in FIG. 3. The sample was prepared by dosing the complex protective material swatch with a total of 6×1 µL VX and using a single 47 mm diameter DVB pad as the sorbent layer. After dosing, the experimental test cell was sealed for 24 hours at 1 psi. Upon completion, the experimental test cell was disassembled, and the DVB pad was individually extracted and analyzed via LC-MS/MS analysis for breakthrough of VX through the complex protective material swatch.

Results for both the experimental test cell for measuring contaminant breakthrough on a complex protective material swatch and the typical LVAP test cell for measuring contaminant breakthrough on a simple protective material swatch are shown in Table 1, below:

TABLE 1

Experimental and Comparative Breakthrough Results

| Test Number | Comparative Breakthrough Results Using Typical LVAP Breakthrough Mass (µg) | Breakthrough Results Using Experimental Test Cell Breakthrough Mass (µg) |
| --- | --- | --- |
| 1 | 15.60 | 14.62 |
| 2 | 13.95 | |
| 3 | 17.39 | |
| 4 | 16.39 | |
| 5 | 14.80 | |
| Average (µg) | 15.63 | N/A |
| Standard Deviation (µg) | 1.34 | N/A |
| Relative Standard Deviation | 8.59% | N/A |

These results indicate that breakthrough results for a complex protective material swatch tested with the experimental test cell fall within the standard deviation of simple material swatches tested with the LVAP apparatus. As such, this test demonstrates that the experimental test cell is capable of producing approximately the same results as a typical LVAP test cell, even though the material swatch tested in the experimental test cell included various complex features.

In a second test, the test cell shown in FIG. 3 was also tested for pressure evenness between the complex protective material swatch and the sorbent pad. Two experimental test cells were constructed according to previously described methods. In the first experimental test cell, memory foam was used as the pressure-generating insert. In the second experimental test cell, nitrile foam was used as the pressure-generating insert. The two experimental test cells were otherwise identical. A pressure sensor was placed between the pressure-generating insert and the complex protective material swatch in each of the experimental test cells in order to generate a pressure array for mapping the interface between the pressure-generating insert and the complex protective material swatch.

The results showed that the memory foam, when used to form the pressure generating insert, produced evenly applied pressure between the pressure-generating insert and the complex protective material swatch at a pressure of 1 psi. However, the nitrile foam, when used as the pressure-generating insert, created uneven pressure and gaps between the pressure-generating insert and the complex protective material swatch throughout the length of the zipper. The presence of gaps and uneven pressure between the nitrile foam pressure-generating insert and the complex protective material suggest that a memory foam pressure-generating insert is superior.

In a final test, the test cell shown in FIG. 2 was tested for leaks. In this test, the experimental test cell was constructed according to previously described methods with an additional impermeable protective layer placed between the sorbent layer and the complex protective material swatch. The sorbent layer included eight evenly spaced 47 mm diameter DVB pads that were cut in half and placed around the perimeter of the sorbent layer. In the test, the experimental test cell was placed into an incubator for 12 hours to reach a thermal equilibrium at 32° C. Upon reaching thermal equilibrium, the complex protective material swatch was dosed with a total of 45 1 µL VX droplets applied across the swatch using a 50 µL Hamilton syringe and a 1:50 repeater. After dosing, the experimental test cell was sealed and the test proceeded for 24 hours at 1 psi.

The purpose of this test was to measure the efficacy of the sealing gasket in its ability to seal the complex protective material swatch from cross contaminating the isolated sorbent layer. Because the sorbent layer was separated from the dosed complex protective material swatch, any detectable contaminant on the sorbent layer would be attributed to cross-contamination from vapor escape or sorbent layer handling. After 24 hours of testing, the test cell was disassembled, and each DVB pad was individually extracted and analyzed via LC-MS/MS analysis for breakthrough of VX through both the complex protective material swatch and the impermeable protective layer. Results from this test are shown in Table 2, below:

TABLE 2

| Gasket Efficacy Results | |
| --- | --- |
| DVB Pad Number | Breakthrough Mass (ng) |
| 1 | <0.4 |
| 2 | <0.4 |
| 3 | <0.4 |
| 4 | <0.4 |
| 5 | <0.4 |
| 6 | <0.4 |
| 7 | <0.4 |
| 8 | <0.4 |

As shown in Table 2, none of the DVB pads yielded measurable VX quantities. In fact, each pad included less than 0.4 nanograms (ng) of breakthrough mass, which was the quantification limit of the analytical instrument used during testing. This test was repeated using the test cell shown in FIG. 3, which achieved the same results listed in Table 2. These results demonstrate that the experimental test cell, according to multiple embodiments, sufficiently sealed the complex protective material swatch so that vapor leaks were prevented.

It should be understood that any two quantitative values assigned to a property may constitute a range of that property, and all combinations of ranges formed from all stated quantitative values of a given property are contemplated in this disclosure.

Having described the subject matter of the present disclosure in detail and by reference to specific embodiments, it is noted that the various details described in the present disclosure should not be taken to imply that these details relate to elements that are essential components of the various embodiments described in this disclosure. Rather, the appended claims should be taken as the sole representation of the breadth of the present disclosure and the corresponding scope of the various embodiments described in this disclosure. Further, it will be apparent that modifications and variations are possible without departing from the scope of the appended claims. More specifically, although some aspects of the present disclosure are identified as particularly advantageous, it is contemplated that the present disclosure is not necessarily limited to these aspects.

What is claimed is:

1. A test cell for measuring permeation of a contaminant through a complex protective material swatch, the test cell comprising:
   a base frame comprising a test slot;
   a pressure-generating insert positioned on a pedestal within the test slot;
   a sealing plate in contact with the base frame;
   an impermeable protective layer in contact with the sealing plate, the impermeable protective layer comprising a flexible material and configured to prevent the contaminant from contaminating the pressure-generating insert;
   a sorbent layer positioned on a top surface of the impermeable protective layer;
   a complex protective material swatch in contact with the sorbent layer;
   a locking frame in contact with the impermeable protective layer and configured to secure the impermeable protective layer to the sealing plate;
   a sealing gasket in contact with at least the locking frame and the complex protective material swatch;
   a gasket compression frame in contact with the sealing gasket, the gasket compression frame configured to compress the sealing gasket between the gasket compression frame and the sealing plate;

a cover in contact with the gasket compression frame, the cover configured to allow for dosing the complex protective material swatch with the contaminant; and one or more weights in contact with the cover, the one or more weights causing evenly pressurized contact between the complex protective material swatch and the sorbent layer in order to determine the level of permeation of the contaminant through the complex protective material swatch.

2. The test cell of claim 1, further comprising a stability plate positioned between the sealing gasket and the cover, the stability plate configured to provide additional structural integrity to the test cell.

3. The test cell of claim 1, wherein the pressure-generating insert comprises viscoelastic polyurethane foam.

4. The test cell of claim 1, wherein the sorbent layer comprises one or more divinyl benzene pads, latex, synthetic skin, or combinations thereof.

5. The test cell of claim 1, wherein the complex protective material swatch comprises a single or double-layer fabric swatch having a zipper, a hook and loop fastener, seams, hems, valve seats, pass-through fittings, electronic connectors, or combinations thereof.

6. The test cell of claim 1, wherein the one or more weights provide from 0.1 pounds per square inch (psi) to 5 psi of evenly pressurized contact between the complex protective material swatch and the sorbent layer.

7. The test cell of claim 1, wherein the impermeable protective layer comprises butyl rubber, nitrite, neoprene, or combinations thereof.

8. The test cell of claim 7, wherein the impermeable protective layer has a thickness from 1 mil to 20 mils.

9. The test cell of claim 1, wherein the contaminant comprises a low-volatility substance.

10. The test cell of claim 1, wherein the base frame further comprises one or more triangular guides configured to allow the test cell to be positioned at a slanted angle.

11. The test cell of claim 1, wherein the one or more weights each comprise a handle and self-locating nubs, the handle providing a gripping point for an operator manipulating the test cell and nubs providing consistent placement of the weights.

12. The test cell of claim 1, wherein the locking frame, the cover, or both comprise one or more self-locating tabs, the one or more self-locating tabs providing a one or more additional gripping points for an operator manipulating the test cell.

13. A method for measuring permeation of a contaminant through a complex protective material swatch, the method comprising:

providing a base frame comprising a test slot, wherein a pressure-generating insert is positioned on a pedestal within the test slot;

placing a sealing plate on the base frame;

securing an impermeable protective layer to the sealing plate with a locking frame;

placing a sorbent layer on the impermeable protective layer;

placing the complex protective material swatch on the sorbent layer;

placing a sealing gasket on at least the locking frame and complex protective material swatch;

placing a gasket compression frame on the sealing gasket;

compressing the sealing gasket between the gasket compression frame and the sealing plate, thereby sealing the test cell;

dosing the complex protective material swatch with the contaminant;

placing a cover on the gasket compression frame;

applying one or more weights to the cover, thereby causing evenly pressurized contact between the complex protective material swatch and the sorbent layer; and measuring a level of contamination of the sorbent pad upon exposure to the complex protective material swatch.

14. The method of claim 13, further comprising positioning a stability plate between the sealing gasket and the cover.

15. The method of claim 13, wherein the pressure-generating insert comprises viscoelastic polyurethane foam.

16. The method of claim 13, wherein the sorbent layer comprises one or more divinyl benzene pads, latex, synthetic skin, or combinations thereof.

17. The method of claim 13, wherein the complex protective material swatch comprises a single or double-layer fabric swatch having a zipper, a hook and loop fastener, seams, hems, valve seats, pass-through fittings, electronic connectors, or combinations thereof.

18. The method of claim 13, wherein the one or more weights provide from 0.1 pounds per square inch (psi) to 5 psi of evenly pressurized contact between the complex protective material swatch and the sorbent layer.

19. The method of claim 13, wherein the impermeable protective layer comprises butyl rubber, nitrile, neoprene, or combinations thereof.

20. A test cell, comprising:

a base frame comprising a test slot;

a pressure-generating insert positioned on a pedestal within the test slot;

an impermeable protective layer in contact with the base frame;

a sorbent layer positioned between the pressure-generating insert and the impermeable protective layer;

a complex protective material swatch in contact with the sorbent layer, the complex protective material swatch having a contaminant applied thereon;

a locking frame in contact with the impermeable protective layer, wherein the locking frame secures the impermeable protective layer to the base frame;

a sealing gasket in contact with at least the locking frame and the complex protective material swatch;

a gasket compression frame in contact with the sealing gasket;

a cover in contact with the stability plate; and one or more weights in contact with the cover.

* * * * *